(12) United States Patent
Ubogaya et al.

(10) Patent No.: US 7,578,322 B2
(45) Date of Patent: Aug. 25, 2009

(54) METHOD AND APPARATUS FOR DISPENSING POWDERED MATERIALS

(75) Inventors: Rivmera Ubogaya, Ocean, NJ (US); Stanislav Valov, Brooklyn, NY (US)

(73) Assignee: Ber-Kle Enterprises, Inc., Brooklyn, NY (US)

( * ) Notice: Subject to any disclaimer, the term of this patent is extended or adjusted under 35 U.S.C. 154(b) by 593 days.

(21) Appl. No.: 11/342,896

(22) Filed: Jan. 30, 2006

(65) Prior Publication Data

US 2006/0196506 A1    Sep. 7, 2006

Related U.S. Application Data

(60) Provisional application No. 60/658,364, filed on Mar. 4, 2005.

(51) Int. Cl.
*B65B 1/20* (2006.01)
(52) U.S. Cl. ............................. 141/71; 141/12; 222/283; 222/404; 425/354; 100/42

(58) Field of Classification Search .................. 141/12, 141/71, 83, 249; 222/190, 282, 283, 287, 222/404, 405, 319; 425/415, 354; 264/120; 100/269.09, 42, 906, 903
See application file for complete search history.

(56) References Cited

U.S. PATENT DOCUMENTS

| | | | | |
|---|---|---|---|---|
| 4,147,489 | A | * | 4/1979 | Milburn et al. ............... 425/355 |
| 4,371,101 | A | * | 2/1983 | Cane et al. ................... 222/636 |
| 5,591,461 | A | * | 1/1997 | Komatsu et al. ............. 425/169 |
| 6,886,612 | B2 | * | 5/2005 | Duffield ...................... 141/284 |

\* cited by examiner

*Primary Examiner*—Timothy L Maust
*Assistant Examiner*—Jason K Niesz
(74) *Attorney, Agent, or Firm*—The Farrell Law Firm, LLP (57) ABSTRACT

A method and apparatus for dispensing powdered material provides for processing a volume of powdered material to be dispensed so that density of the processed material is modified to substantially uniform density, and further for distributing multiple dosages of the powdered material in a time-efficient, precise manner.

12 Claims, 9 Drawing Sheets

METHOD AND APPARATUS FOR DISPENSING POWDERED MATERIALS

PRIORITY

This application claims the benefit under 35 USC §119 to a provisional patent application titled "Method And Apparatus For Dispensing Powdered Materials" filed in the US Patent and Trademark Office on Mar. 4, 2005 and assigned Ser. No. 60/658,364, the contents of which are incorporated herein by reference.

BACKGROUND OF THE INVENTION

1. Field of the Invention

The present invention relates to methods and apparatuses for dispensing powdered material. More particularly, the invention relates to methods and apparatuses for dispensing of powdered material in a time-efficient, precise manner.

2. Description of Related Art

Numerous industries, including, among others, pharmaceutical and medical industries, frequently deal with minute quantities of powdered material. Accordingly, efficiency and accuracy of dispensing apparatus has become particularly important. However, the majority of the known powder dispensers fall short of satisfying the needs of the market.

The main criterion defining the accurate dispensing of powdered material is the uniform weight of multiple dosages of the powdered material. The weight of the dispensed powdered material is directly proportional to its dispensed volume and density. Typically, a volume of powdered material is presumed to have its known true density, which is thus often viewed as a constant during dispensing of multiple dosages of the powdered material. Based on this premise, many of the known apparatuses rely on controlling the flow of powdered material to attain the uniform weight of multiple dispensed dosages. For many types of powdered material, however, even distribution of particles in a given volume and therefore the density of particles in this volume are far from being uniform. As a consequence, quite often the weight of individual dosages of powdered material may vary from dosage to dosage. Needless to say, even miniscule deviations of the weight of the dispensed dosage of powdered material, used, for example, for drug preparation, from the target weight may result in serious negative effects.

Due to the complex nature of powdered materials, it is difficult to ascertain the flow properties of a given powdered material which causes processing difficulties. Apparently identical powdered materials may vary from batch to batch or supplier to supplier. Transportation conditions can dramatically alter the packing condition from a highly aerated state at one extreme to a hard-consolidated condition at the other. Free-flowing powders may be prone to segregation, attrition and electro-static charge. Attrition for example can change particle shape, remove surface coatings, produce fines and result in bulk density changes.

Powders may be unintentionally changed during storage, handling and processing. In storage, for example, powders may consolidate under their own weight; during transportation, vibration can produce a similar or even worse level of solidification; and during processing, while powdered material flows from a powder-containing vial through a material processing mechanism into a material-receiving vial, particles may either adhere to guiding surfaces or agglomerate around the adhered particles, gradually reducing and eventually affecting the flow uniformity. Furthermore, some types of powdered material can be compacted under their own weight thereby affecting density along the column of the stored powdered material with relatively low density at the top of the column and relatively high density at the bottom thereof.

Thus, efficient processing of powdered materials depends upon flow rates, levels of compaction, vibration levels, the head of material in a hopper type of conveying surface and environmental conditions. All these factors are important in determining the consistency and efficiency of processing. Attaining the uniform density of powdered material to be dispensed in multiple dosages may drastically affect the importance of these difficult to control factors. While numerous attempts have been directed to controlling, for example, flow rates, density control has been largely ignored. As a result, accurate and rapid dispensing of powdered materials remains problematic, particularly in industries dealing with minute amounts of powdered material.

SUMMARY OF THE INVENTION

The present invention includes a method of delivering a volume of powdered material to a dispensing chamber. Powdered material occupying the geometric space of the dispensing chamber, as a rule, is characterized by bulk density different from true density of this material due to interior voids, cracks or pores filled with pockets of air. Distribution of the air pockets over the entire volume of material to be dispensed is uneven. Bulk density only equals true density when there are no internal openings in the stored material. In accordance with the invention, to minimize the difference between the bulk and true densities, the stored material is compacted by displacing the first of two opposing compactors within the dispensing chamber towards the second compactor. Air is forced out of the dispensing chamber through a specifically designed outlet. As a consequence, the openings, previously filled with air, receive powdered materials, and the envelope of the compacted powdered material has substantially uniform density approaching the known true density of this material.

After providing the stored material with substantially uniform density, the inventive method allows for formation of a material-free area above a top level of compacted material by controllably and selectively displacing one or more of the compactors and guide. As a result, the material-free area has a predetermined dispense volume receiving an amount of material, which is displaced into this area by the first compactor, sufficient to meet the desired target weight. Further displacement of the material from the just-filled area into a material-dispensing chamber completes the inventive process.

In accordance with an exemplary embodiment of the invention, the dispense volume of the material-free area is controlled by displacing the second compactor above the top level of the compacted material at a predetermined distance or height. The predetermined distance is determined so that when the first compactor again moves towards the second compactor at the same predetermined distance, the previously formed material-free area is filled with the desired amount of material. This desired amount corresponds to the target weight of each dosage of the powdered material to be dispensed.

Subsequently, the second compactor is displaced away from the first compactor. Displacement of the second compactor clears a passage leading from the material-dispenser chamber to the material-distribution chamber. A guide, configured to move along the passage perpendicular to displacement of the compactors, is then actuated to displace the desired amount of the powdered material toward the distribution chamber.

In accordance with another exemplary embodiment of the invention, the dispense volume is controlled by displacing the second compactor at a predetermined distance to form a material-free area subsequently filled with an initial amount of material. This amount of material is further delivered to the material-distribution chamber, where its weight is first determined and then compared to the target weight. If the determined weight has not reached the desired target weight, a new dispense volume is formed by controllably actuating the guide after the second compactor is again displaced at the predetermined distance. Thus, a new material-free area is smaller than the initial one and has a dispense volume corresponding to an additional amount of material to be added to the initial amount of material. The above-described sequence of operations continues until the cumulative weight of the dispensed material is at least equal to the target weight.

An apparatus for carrying out the inventive process includes a dispensing chamber defined between the opposing surfaces of the compactors or plungers, which are displaceable along the same linear path. The guide, pushing the predetermined amount of the powdered material towards the powder distribution chamber, moves transversely to the linear path of the plungers.

In accordance with yet another exemplary embodiment, the apparatus may operate under the control of a central processing unit (CPU). The CPU issues a sequence of commands causing the first and second plungers to move the desired distance. The desired distance is calculated in response to input data including true density of powdered material to be dispensed, dispense volume of the material-free chamber, and target weight of each dosage of the material.

As a dosage is delivered to the powder distribution chamber, its weight may be actually determined. If the target weight has not been attained, a feedback signal indicating the determined weight of the dosage is input into the CPU. Upon processing the feedback signal, the CPU generates a control signal causing displacement of one or more actuators and guide at a newly calculated distance to form a new material-free area. This area has a dispense volume sufficient to receive an additional amount of material further added to the previously dispensed dosage to meet the target weight.

The inventive method characterized by uniform density of powdered material, which is stored, for example, in a material-dispensing chamber, provides for an even distribution of powdered particles in the entire volume, stable flow rate and accurate distribution of multiple dosages of powdered material. The apparatus has a simple structure with a few elements that can be rather easily manufactured and maintained.

These and other features and aspects of the present invention will be better understood with reference to the following description, figures, and appended claims.

BRIEF DESCRIPTION OF THE DRAWINGS

The above features and advantages of the present invention will be more readily apparent from the following detailed description, taken in conjunction with the accompanying drawings, in which.

DETAILED DESCRIPTION OF THE PREFERRED EMBODIMENTS

Reference will now be made in detail to several exemplary embodiments of the invention that are illustrated in the accompanying drawings. Wherever possible, same or similar reference numerals are used in the drawings and the description to refer to the same or like parts or steps.

Figure 5:
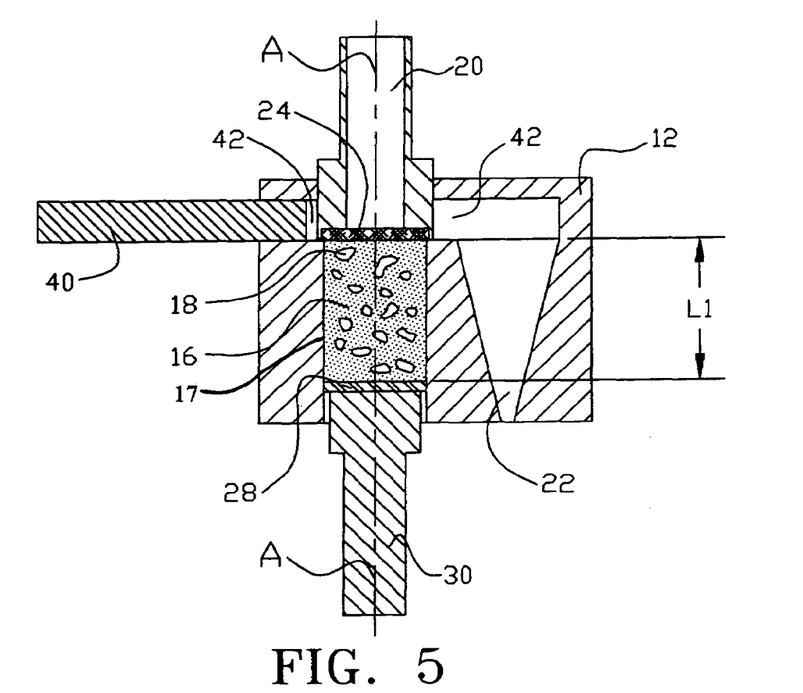
FIG. 5 is a sectional view of the inventive apparatus taken along lines V-V, as seen in FIG. 3, and illustrating an initial volume of powdered material with pockets of air.
Figure 6:
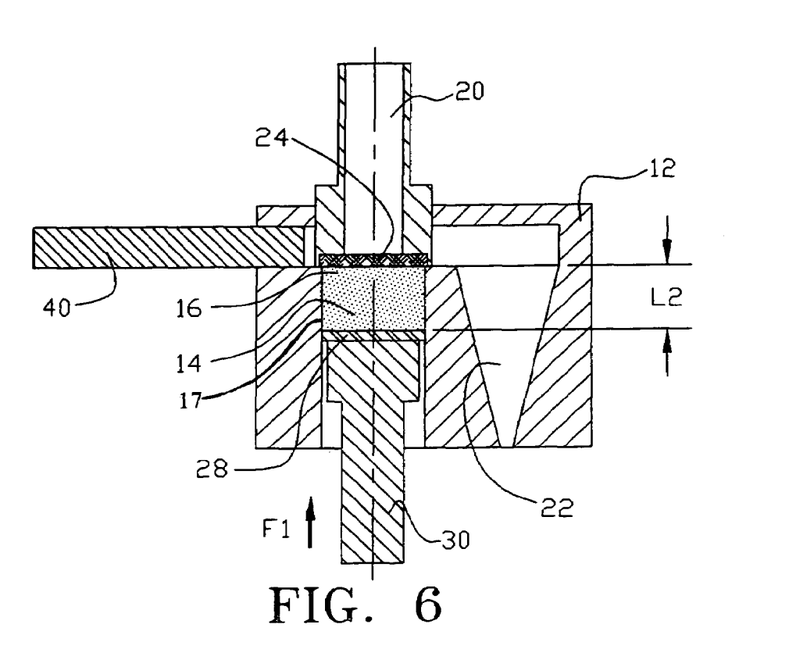
FIG. 6 is a sectional view of the inventive apparatus analogous to the view illustrated in FIG. 5, but illustrating the compacted powdered material having a substantially uniform density upon evacuating the pockets of air.

Referring to FIGS. 1-8 and 17, an apparatus 10 for dispensing powdered material is configured with a body 12 having a dispensing chamber 17 (FIGS. 4-8) for receiving a volume of powdered material 16. Initially, the received powdered material has a plurality of air pockets 18 (FIG. 5) unevenly distributed between particles. Distribution and quantity of air pockets are unpredictable variables contributing to non-uniform density of the received volume of material. Elimination of air pockets 18 leads to powdered material 16 having a substantially uniform density, as shown in FIG. 6.

To realize degassing of the stored volume of powdered material 16, the inventive apparatus 10 employs first and second plungers 20, 30 (FIGS. 1-8) provided in the dispensing chamber 17 and operative to move relative to one another along a common axis A-A (FIG. 5). Initial displacement of one of the first and second plungers 20, 30 towards the other reduces an initial distance L1 (FIG. 5) between the opposing surfaces of the plungers 20, 30 to a distance L2 (FIG. 6) and causes compaction of the stored material. Compaction of the material is accompanied by air evacuation through a perforated or porous plate 24 coupled to one of the plungers and serving as a material-forming surface. The plate 24 includes multiple orifices shaped and dimensioned to block powdered particles while providing unhindered passage of air. As a result, as shown in FIG. 6, the stored material occupies a smaller volume 14, as compared to the one of FIG. 5. Most importantly, the compacted material has substantially uniform density.

Figure 7:
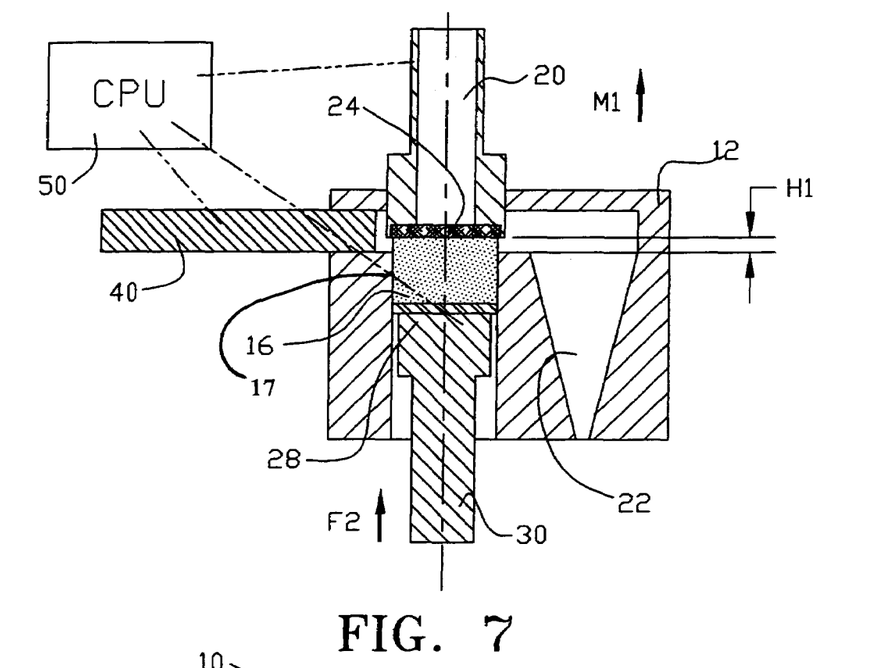
FIG. 7 is a sectional view of the inventive apparatus analogous to the view shown in FIGS. 5 and 6 and illustrating an operational step of forming the desired amount of powdered material to be dispensed, during which both compactors move in a sequential manner at the predetermined distance H1.
Figure 17:
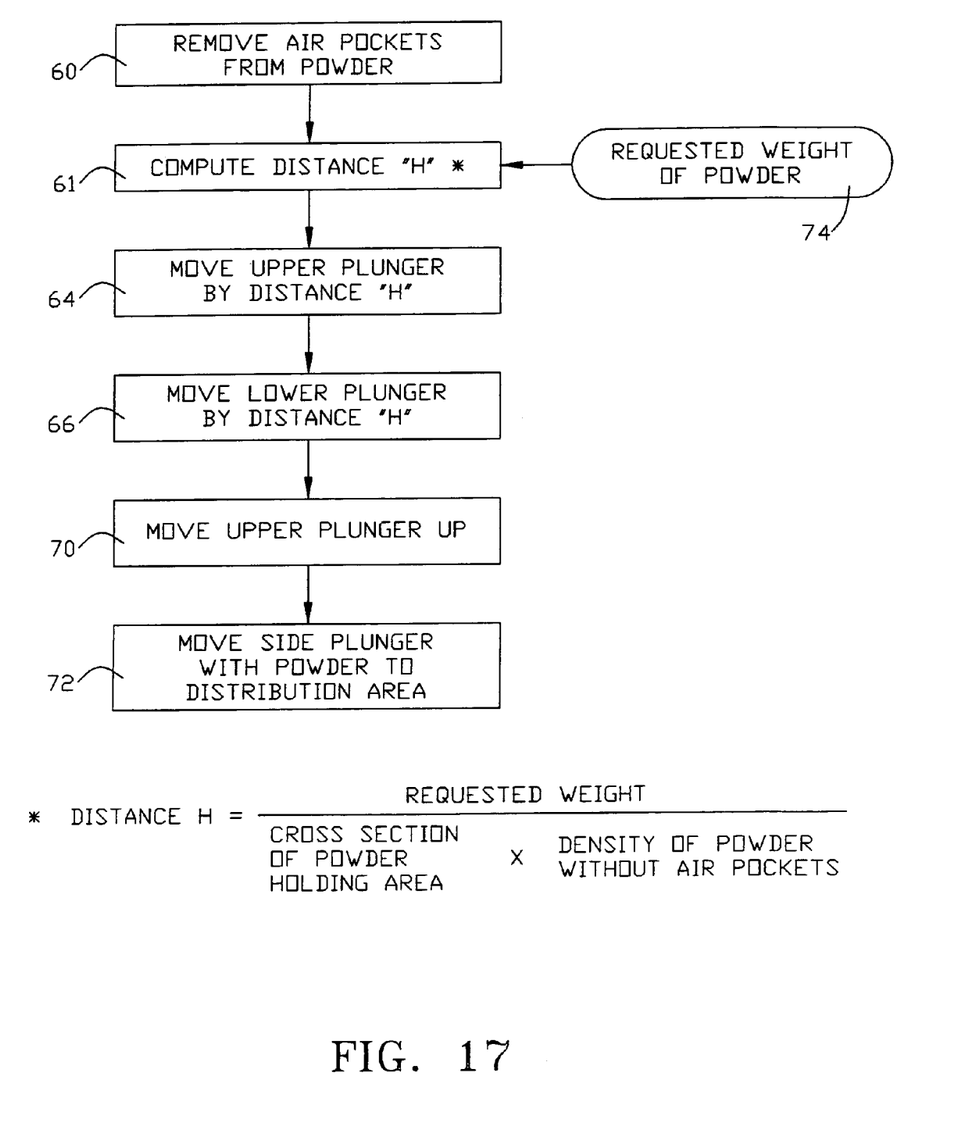
FIG. 17 is a flow chart illustrating the inventive method, which is carried out by the apparatus of the present invention.

The powdered material having the substantially uniform density, which is characterized by uniform distribution of powder particles across the dispensing chamber 17, facilitates further dispensing of multiple dosages of the stored material, which thus have substantially uniform weight. A central processing unit (CPU) 50 (FIGS. 7-8) generates a control signal input in one of plunger actuators 104, 106 (FIG. 2) responsible for controlled displacements of the plungers 20, 30, respectively. After the plungers have reached a position shown in FIG. 6, one of these plungers, for example the plunger 20, is displaced at a distance H1 (FIG. 7) away from the top level of the compacted material to form a material-free area. Determination of the distance H1 is based, among others, on a target weight of individual dosages of material to be dispensed. Turning to FIG. 17, the distance H is a function of the target weight, cross section of the material-free area to be subsequently filled with the powdered material and density of this material, which is known and substantially uniform across the stored volume of material. Inputting all these parameters into the CPU 50 and further processing them in accordance with a specifically designed algorithm will generate a control signal in response to which the actuator 106 will displace the plunger 20 at the desired distance H1, as shown in FIG. 7.

Displacement of the plunger 20 creates the material-free area having a predetermined dispense volume, which can be filled with a precise amount of powdered material corresponding to the target weight of the dosage of this material to be dispensed. Filling the previously formed material-free area is realized by subsequent displacement of the plunger 30 towards the plunger 20 at the same distance H1 or slightly greater. Although a dosage of material filling the material-free area would not have the target weight, weight of material forming an additional dosage will be calculated so that the cumulative weight of the initial and subsequent dosages corresponds to the target weight.

Figure 8:
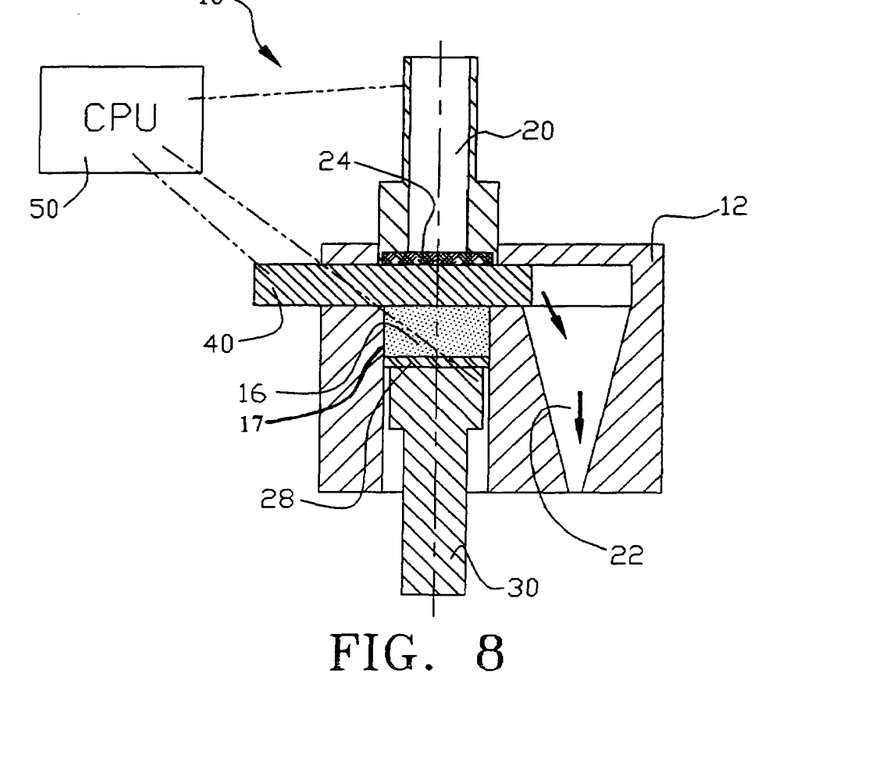
FIG. 8 is a sectional view of inventive apparatus similar to FIG. 7 and illustrating an operational step, during which the predetermined amount of powdered material is delivered to a material-distribution chamber.

As shown in FIGS. 5 and 6, the plunger 20 occupies a predetermined position in which the perforated plate 24 is aligned with a bottom of a passage 42 (FIG. 5). The passage 42 is provided in the body 12 and shaped to slidably receive a third plunger or guide 40 displaceable perpendicular to the linear path of the plungers 20 and 30. In this predetermined position, the plunger 20 with the plate 24 completely blocks the passage 42 and therefore comprises an end cover of the material dispensing chamber 17 to prevent flow of powdered material from the material-dispensing chamber 17 to a material-distribution chamber 22. Depending on the target weight of the dosage of material, the plunger 20 moves across the passage 42 at the distance H1 to create the material-free space or area. After displacing the plunger 30 at the same predetermined distance so that this space is filled with a predetermined amount of material, the plunger 20 is again moved away from the plunger 30 so as to completely clear the passage 42. Plunger 30 acts as a chamber plug which comprises a second end cover of the material dispensing chamber 17. Finally, the CPU 50 generates a further signal enabling an actuator 102 (FIG. 2) to move the guide 40 displacing the amount of material, which has filled the previously formed material-free space, toward the material-distribution chamber 22, as illustrated in FIG. 8.

Figures 1, 2, 3, 4:
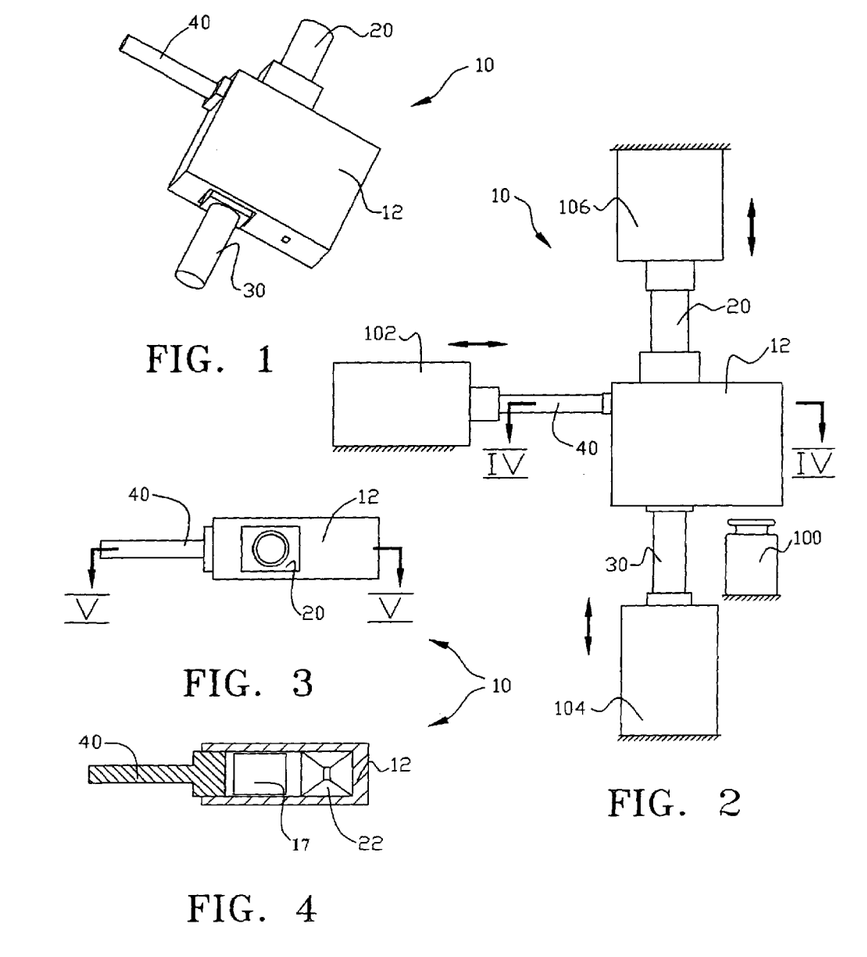
FIG. 1 is an isometric view of an apparatus for dispensing powdered material configured in accordance with one embodiment of the invention.
FIG. 2 is a front view of the inventive apparatus.
FIG. 3 is a top view of the inventive apparatus of FIGS. 1 and 2.
FIG. 4 is a cross-sectional view of the inventive apparatus taken along lines IV-IV, as illustrated in FIG. 2.

Configuration of the apparatus 10 can vary as long as the above-discussed method is at work. Thus, for example, the porous or perforated plate 24 may be coupled to the plunger 30. The plunger 40 can also be mounted to the body 12 so as to transverse the passage 42 blocked by the plunger 30, not by the plunger 20. The dispensing chamber 17 may have a polygonal or circular cross-section. According to an exemplary embodiment of the invention, the distribution chamber 22 may narrow towards its outlet juxtaposed with a powder-receiving container 100 (FIG. 2). Providing the distribution chamber 22 with a Venturi-type configuration, which typically has an intermediate narrow region located between opposite relatively wide inlet and outlet regions, may improve aerodynamic characteristics of the powder flow. Shapes and dimensions of the plungers 20, 30 and 40 are configured to correspond to shapes and dimensions of the dispensing chamber 17 and passage 42. One of the plungers 20 and 30 can be provided with a gasket 28 sealingly sliding along the inner surface of the dispensing chamber 17. Further modification of the apparatus 10 may include simultaneous displacement of the plungers 20 and 30 at the distance H1. In this case, the apparatus 10 further has a clutch disengaging the plungers 20 and 30, when the plunger 20 has to clear the passage 42. The actuators 102, 104 and 106 (FIG. 2) are linear programmable or non-programmable actuators selected from servomotors, step motors, pneumatic or hydraulic actuators. The CPU 50 is preferably a processor provided with executable programs running the above-discussed sequence of operations of the apparatus 10. Alternatively, of course, the CPU 50 may be configured as a combination of hardware elements fully capable of controlling the operation of the apparatus 10 according to the desired sequence. Implementation of multiple flow and weight sensors is, of course, possible and can be realized by artisans in a rather conventional manner.

FIG. 17 is a flow chart of a method for operating the apparatus 10 in accordance with an exemplary embodiment of the invention. It starts with filling the dispensing chamber 17 with a volume of material characterized by non-uniform density. Subsequently, the air pockets unevenly distributed across the column of the stored material are evacuated upon displacing the plungers 20 and 30 relative to one another (step 60). Further, the distance H1, at which one of the plungers 20, 30 should be displaced to form the desired dispense volume of the material-free space, is calculated in response to inputting the target weight (steps 61 and 74). Subsequent displacement of the other one of plungers 20, 30 at the same distance H1 illustrated by steps 64 and 66, leads to filling the previously material-free space with the amount of material, which corresponds to the target weight (step 70). If the third plunger 40 is initially spaced from the dispensing chamber 17, as shown in FIGS. 5 and 6, then this plunger moves at such a distance that its end surface is aligned with the inner surface of the dispensing chamber 17 (step 72). Alternatively, the third plunger 40 may be initially positioned so its end surface is flush with the inner surface of the dispensing chamber 17. Subsequently, the plunger 20 is displaced again at a distance sufficient to clear the passage 42, which provides flow communication between the dispensing and distribution chambers 17 and 22. Finally, the third plunger 40 is actuated to guide the desired amount of material filling the previously formed material-free space toward the distribution chamber 22 (step 72).

FIGS. 9-16 and 18 illustrate another exemplary embodiment of the invention directed to an apparatus 150 for dispensing powdered material 170 configured to create a material-free area by controlling displacement of one of plungers and a guide and to provide a powdered material stored in the dispensing chamber 17 of the apparatus 150 having a substantially uniform density (FIGS. 1-8).

Figures 9, 10:
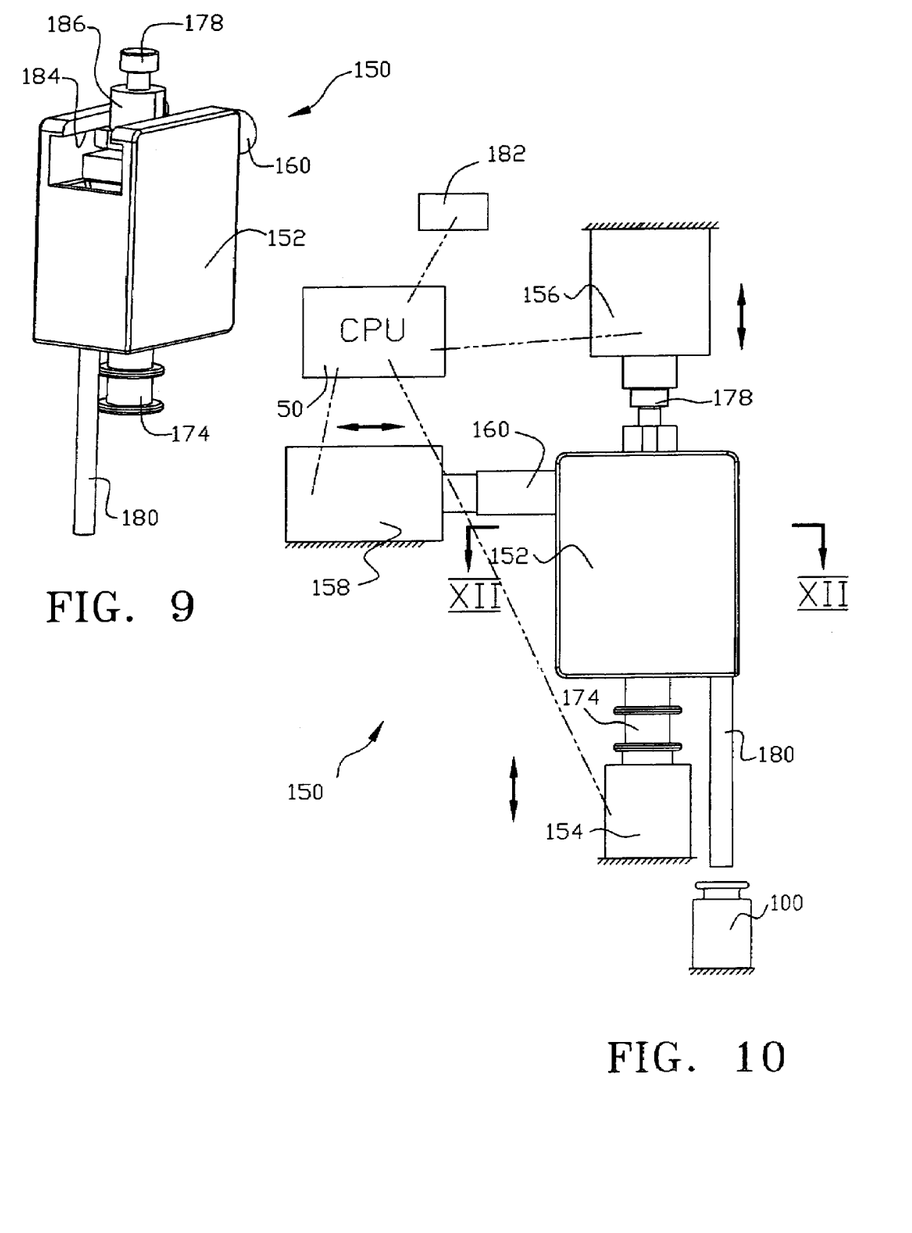
FIG. 9 is an isometric view of the inventive apparatus configured in accordance with an other exemplary embodiment of the invention.
FIG. 10 is a side elevational view of the apparatus of FIG. 9.
Figure 11:
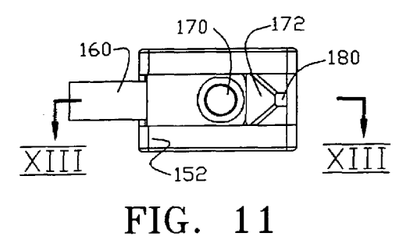
FIG. 11 is a top view of the apparatus illustrated in FIG. 9.
Figure 12:
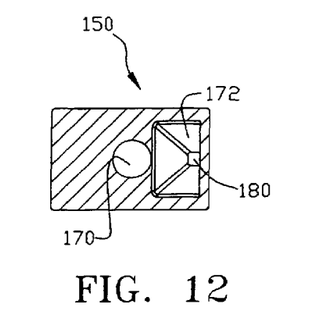
FIG. 12 is a cross-sectional view of the inventive apparatus taken along lines XII-XII, as seen in FIG. 10.
Figure 13:
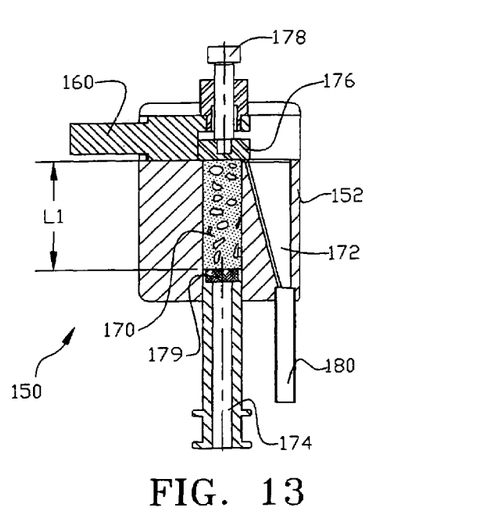
FIG. 13 is a sectional view taken along lines XIII-XIII, as seen in FIG. 11, and illustrating a volume of powdered material, having a non-uniform density caused by the presence of numerous air pockets.

The apparatus 150 illustrated in FIGS. 9-10, like the apparatus 10, is configured with a body 152, two actuators 154 and 156 that displace respective plungers 174, 178 relative to one another in one plane and a third actuator 158. The latter moves a third plunger or guide 160 in a plane extending transversely to the plane of plungers 174 and 178. The body 152 has a material-dispensing chamber 170 (FIGS. 11-16) receiving a volume of powdered material with unevenly distributed air pockets, which contribute to non-uniform density of the material, as illustrated in FIG. 13. The material-dispensing chamber 170 is shaped and dimensioned to allow the plunger 174 to reciprocally move along the inner surface of this chamber towards and away from a forming plate 176 fixed to the plunger 178. Accordingly, the plunger 178 and forming plate 176 thus move synchronously with one another. Displacement of the plunger 174 toward the forming plate 176 forces air pockets to escape from the material 170 through a perforated plate 179, fixed to the plunger 174 (FIGS. 13, 14), and through the interior of the plunger 174. Perforations are shaped and dimensioned to provide free airflow, but prevent powdered particles from escaping the dispensing chamber. As a result of plunger's displacement, the compacted material 170 has substantially uniform density across its entire volume in the material-dispensing chamber, as illustrated in FIGS. 13-16.

Figure 14:
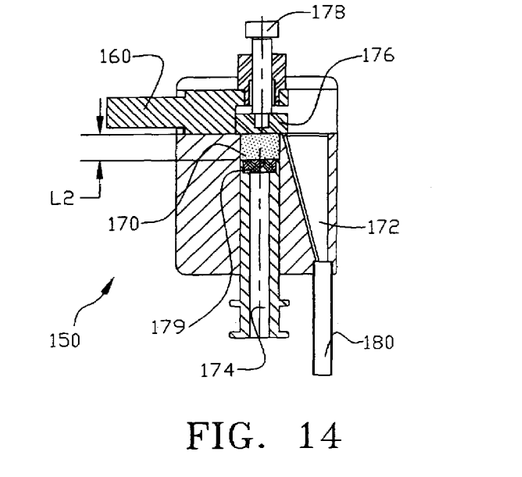
FIG. 14 is a sectional view similar to the view of FIG. 13, but illustrating the volume of the material upon compaction and having a substantially uniform density.
Figure 15:
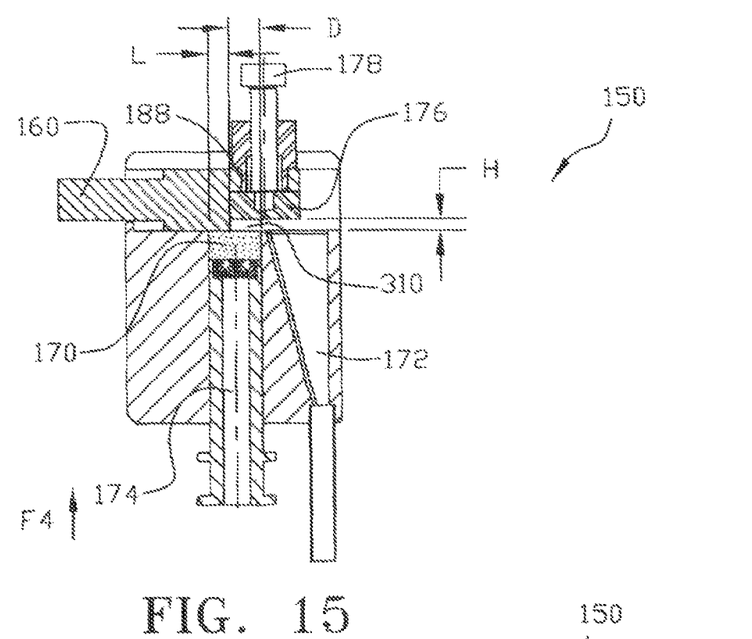
FIG. 15 is a sectional view taken along lines XIII-XIII, as shown in FIG. 11, and illustrating an operational step of forming the void of the volume that corresponds to the predetermined amount of powdered material.

Turning to FIGS. 13-16, after the material 170 is provided with a substantially uniform density, the plunger 178 and forming plate 176 completely block communication between the dispensing chamber 170 and a material-distributing area 172 in its initial position shown in FIGS. 13, 14. Similarly to the apparatus 10, the plunger 178 and the forming plate 176 are moved at a predetermined distance H (FIG. 15). Due to the specifics of any given powder, it is more practical to control the volume of the material free area by reducing its cross-section. This is accomplished by controllably displacing the guide 160 at a distance L (FIG. 15). The numerical values of the height H and distance L are, of course, selected so that the desirable volume of void 310 can receive the desirable amount of material.

Figure 16:
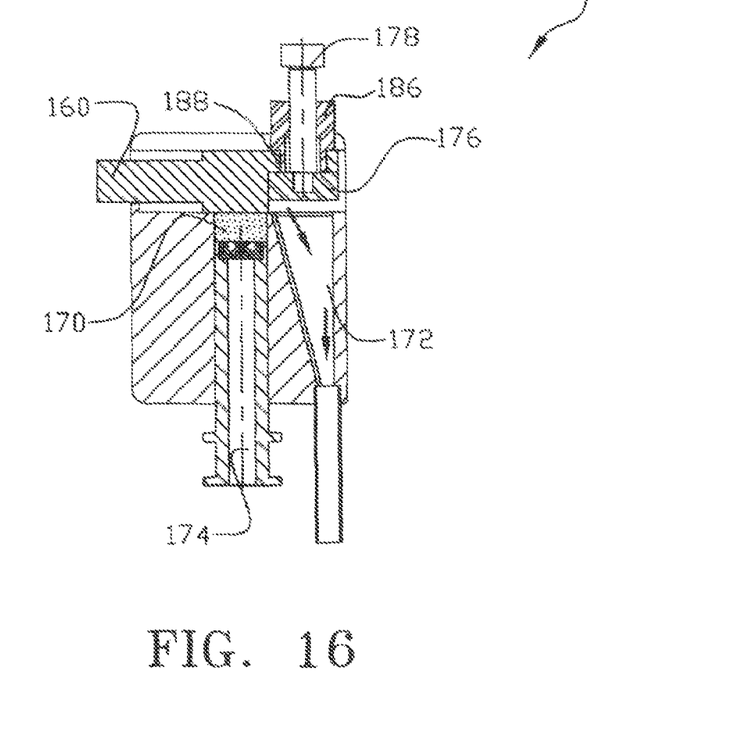
FIG. 16 is a sectional view similar to the view of FIG. 15 and illustrating an operational step of discharging the predetermined amount of powdered material into a powder holding area.

Subsequently guiding the plunger 174 at the height H displaces the desired amount of material corresponding to the target weight from the chamber 170 into the previously formed void 310. Finally, the plunger 178 is moved again to clear a powder passage subsequently traversed by the guide 160 delivering the desired portion of material into the material-distributing chamber 172 (FIG. 16).

As the dispensed dosage of material flows into the material-distributing chamber 172, it may be further dispensed into the powdered container 100 (FIG. 10) through a tube 180 (FIGS. 10-14). The tube 180 has one end of its ends removably or permanently inserted into the outlet of the chamber 172 and the opposite end in flow communication with the container 100.

Mechanically, the apparatus may have various structures allowing it to operate in effective, time-efficient manner. The body 152 of the apparatus 150 includes a pair of linear guides 184 (FIG. 9) engaging a sleeve 186, which slidably receives the plunger 178. The sleeve 186 and the guide 160 (FIG. 5) have complementary formations engaging one another for synchronous displacement in response to displacement of the guide 160. The example, the sleeve 186 may have a recess 188 (FIGS. 15 and 16) receiving protrusions formed on the front end of the guide 160 and conversely. Such engagement prevents relative displacement of the sleeve 186 and the guide 160 when the plunger 178 and the forming plate 176 move towards or away from the opposing plunger 174 to form the material-free area.

Displacing the guide 160, the sleeve 178 and forming plate 176 along a guide path at the distance L, leads to the formation of the material-free area for an additional dosage of material. Note that what is controlled here is a dispense volume of the material-free area. The sequence of displacement of the plunger 178 and guide 160 can be reversed by initially displacing the guide 160. Furthermore, the distance H, at which the plunger is displaced, may differ from the minimum distance selected as a function of the structural specifics of the apparatus 150. The desired volume of the void 310 can be then established by displacing the guide 160 at a distance L. Similarly, the distance L covered by the plunger 160 can be a minimum of maximum and serve as a reference value for establishing the desired volume of the void 310. To do so, the distance H, at which the plunger 178 is subsequently displaced, is controllably modified.

Figure 18:
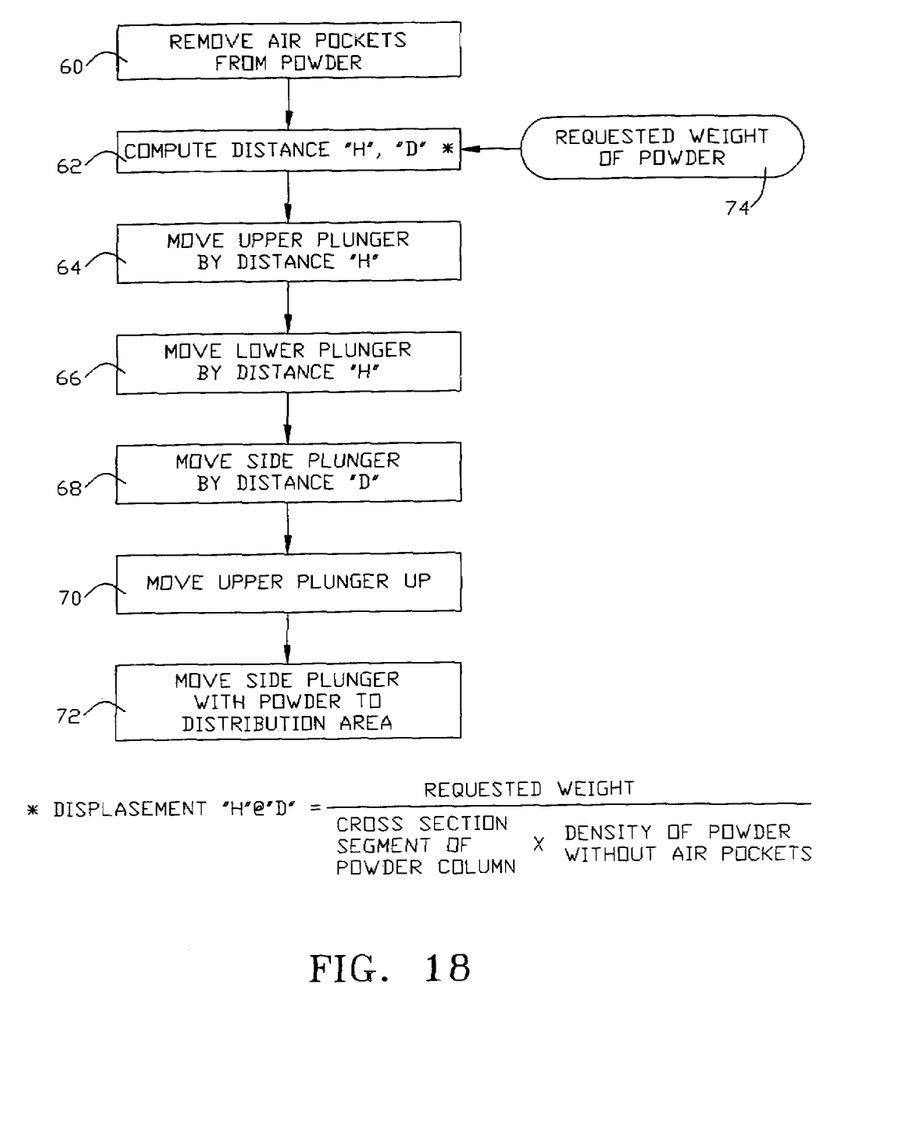
FIG. 18 is a flow chart illustrating the inventive method, which is carried out by the apparatus of the present invention.

Referring to FIG. 18, a method to carry out by the above-disclosed operation of the apparatus 150 begins with removing unevenly distributed air pockets from material stored in the material-dispensing chamber 170 (step 60). Upon inputting the required weight of the portion to be delivered to the material-distributing chamber 172 (FIGS. 13, 14), a CPU 50 computes the distances H and L at which the plunger 178 and guide 160 are to be displaced (steps 62 and 74). Further, the plunger 178 and guide 160 are moved at the calculated distance (steps 64 and 66), to form the void 310 characterized by the desired volume. The volume of void 310 is calculated as H×D, wherein D is the diameter of the dispensing chamber 17 is reduced by the distance L.

Moving the plunger 178 out of the path of the guide 160 after the desired volume has been filled with the predetermined amount of material, the guide 160 displaces this amount to the material-distributing chamber 172 (steps 68, 70 and 72). The desired volume of the material-free area is calculated with the formula used in the apparatus 10 of FIGS. 1-8.

Similarly to the apparatus 10 of FIGS. 1-9, the third plunger or guide 160 can cooperate with either one of the plungers 174, 178. Obviously, the positions of the forming and perforated plates 176 and 179, respectively, can be reversed. Cross-sections of the material-dispensing and material-distribution chambers can vary. As shown in FIGS. 11-16, the material-distribution chambers may have a generally right triangular cross-section. Utilization of servomotors or step motors as plunger actuators 154, 156 and 158 is particularly advantageous due to extremely small distances envisioned for the use of the apparatus 150.

The apparatus 150 may also be used in situation when the type of material to be dispensed and/or its physical parameters are not known. In an exemplary embodiment illustrated in FIGS. 1-16, material identification and, therefore, its physical parameters, such as true density, are known. In contrast, in accordance with another exemplary embodiment illustrated in FIG. 19, the apparatus 150 dispenses substantially uniform dosages or a precise single dosage while no data regarding physical parameters or even the identification of material is available.

This is accomplished by setting a minimal dispense volume of material-free area regardless of material to be dispensed and further, after the dosage of material has filled this material-free area and delivered to the material-distribution area 172, the dispensed dosage is weighted. The minimal dispense volume of the material-free area corresponds to a mechanical threshold below which the apparatus 150 is simply ineffective.

Turning back to FIG. 10, the apparatus 150 further has a weight sensor 182 coupled to the CPU 50 and configured to determine the weight of the dispensed dosage. Of the target weight that has not been attained, the sensor 182 generates a feedback signal corresponding to the actual measured weight received by the CPU 50.

If the determined weight is lower than the target weight, an additional dosage of material is then supplied. Based on the algorithm disclosed below, the apparatus 150 operates to controllably modify the cross-section of the previously set material-free area so that the required additional dosage of material is added to the previously dispensed dosage to meet the target weight. The cross-section of the material-free area and therefore its dispense volume is modified by controllably displacing the guide 160, while having the plunger 178 displaced at the minimal distance H.

Typically, in medical and pharmaceutical industries chemical characteristics of powdered substances are much better known than physical characters. The latter, as mentioned above, is a function of many difficult to control environmental and other parameters. Accordingly, the apparatus operator, assuming that he/she knows the type of material, simply cannot control conditions under which a bulk of this material has been stored or the way it was distributed among smaller vials. Thus, if the operator deals with the same material delivered to the material dispensing chamber from different vials or even from the same vial, the physical parameters may vary from vial to vial as well as from one loading of material to the next one. Accordingly, although creation of electronic library of physical parameters of powdered materials is possible, its practical application is doubtful because of numerous difficult to control factors. In contrast, the apparatus 150 is configured to operate independently of these factors.

Figure 19:
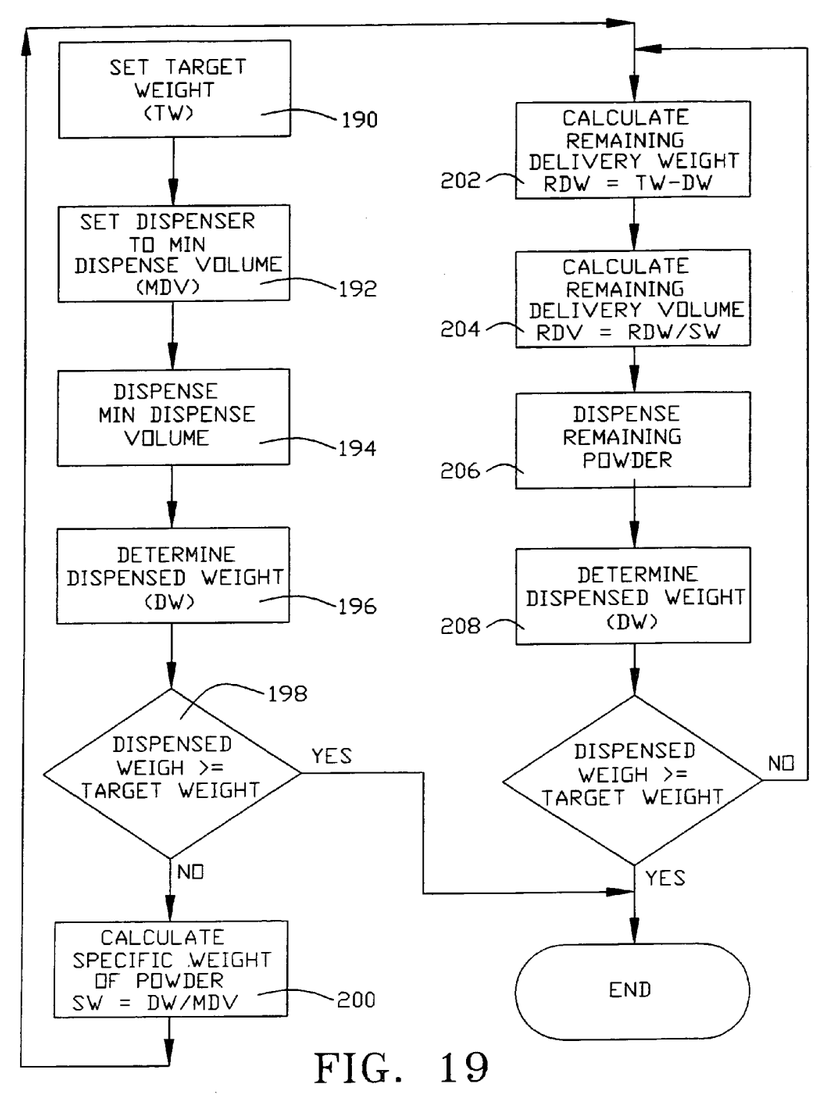
FIG. 19 is a flow chart illustrating an alternative sequence of operations in accordance with yet another exemplary embodiment of the inventive method.

As shown in FIG. 19, having set the target or required weights, as illustrated by a step 190, the plunger 178 (FIGS. 13-16) is displaced to its initial position, in which the bottom of the forming plate 176 is aligned with the bottom segment of the third plunger 160. Compacting the material in the material-dispensing chamber 170, which is realized by displacement of the plunger 174 and the perforated plate 179 towards the forming plate 176, is followed by forming a material-free area (step 192). During this step, the plunger 174 moves within the sleeve 186 (FIGS. 9, 16) at the minimal distance H to form the material-free area above the top level of the compacted material. The area thus has the minimal dispense volume ready to receive a dosage of material. Subsequently displacing the plunger 174 at the same distance H causes material to fill the material-free area. Finally, the guide or third plunger 160 is actuated displacing the sleeve 186, plunger 178 and forming plate 176, as well as material from the material-free area towards the material distribution chamber 172 (step 194).

Determination of the weight of the dispensed dosage of material is realized by any known means (step 196). If the dispensed weight is at least equal to the target weight, as determined (step 198), the process ends.

If the determined weight of the dispensed material is lower than the target weight, the CPU 50 operates in accordance with the following algorithm. Initially, the dispensed dosage of material, having substantially uniform density, is processed to determine its specific weight (step 200). The specific weight (SW) is determined in accordance with the following formula:

$$SW = DW/MDV,$$

wherein DW is the determined weight of the dispensed dosage, and MDV is the minimal dispense volume of the material-free area.

After the remaining weight of the additional dosage is determined as the difference between the target weight and weight of the dispensed initial dosage of material (step 202), the new (remaining) dispense volume (RDV) of the material-free area is determined in accordance with the following formula:

$$RDV = RDW/SW,$$

wherein RDW is the calculated remaining weight of the additional dosage, and SW is the calculated specific weight (step 204).

Having determined the new dispense volume, the guide 160 is moved at the distance L thus diminishing the dispense volume of the material-free area, subsequently filled with the desired amount of material, which is further delivered to the material-distributing chamber 172 (step 206). Upon weighing again the previously and newly delivered amount of material and determining whether the target weight has been reached (step 208), the process either ends, or, if the determined weight is still lower than the target weight, the process returns to step 202 and the sequence is repeated.

The inventive apparatus and methods provide for a more efficient use of powder, reduce stoppages and optimize throughput. Above all, the product quality is substantially improved.

Many additional modifications are intended in the foregoing disclosure, and it will be appreciated by those of ordinary skill in the art that in some instances some features of the invention will be employed in the absence of a corresponding use of other features. The illustrative example therefore do not define the metes and bounds of the invention and the legal protection afforded the invention, which function is served by the claims and their equivalents.

What is claimed is:

1. An apparatus for dispensing at least one dosage of powdered material, the apparatus comprising:

a body having a channel defining a material-dispensing chamber for receiving a predetermined amount of powdered material;

a plunger provided at one end of the channel, reciprocally movable along an inner surface of the channel, constituting a first of two end covers of the material-dispensing chamber;

a chamber plug provided at an end of the channel opposite to the plunger, constituting a second of two end covers of the material-dispensing chamber; and a perforated screen coupled to at least one internal surface of the material-dispensing chamber, wherein a clutch is connected between the plunger and chamber plug for simultaneous displacement of the plunger and chamber plug.

2. An apparatus for dispensing at least one dosage of powdered material, the apparatus comprising:
- a channel of a material-dispensing chamber for receiving the powdered material;
- a plunger moveable within said channel forming a first end cover of the chamber;
- a plug covering an opposite end of the chamber;
- a screen coupled to an internal surface of the chamber; and
- a clutch being connected between the plunger and chamber plug for simultaneously displacing the plunger and chamber plug.

3. The apparatus for dispensing at least one dosage of powdered material as set forth in claim 2, further comprising:
- a pusher provided in a passage of a body of the apparatus,
- wherein the passage is provided in the body and shaped to slidably receive the pusher being displaceable perpendicular to a linear path of the plunger and chamber plug.

4. The apparatus for dispensing at least one dosage of powdered material as set forth in claim 3, further comprising:
- a forming plate fixed to the chamber plug; and
- a perforated plate fixed to the plunger,
- wherein the chamber plug and forming plate move simultaneously with one another.

5. The apparatus for dispensing at least one dosage of powdered material as set forth in claim 3, further comprising:
- a first actuator connected to the chamber plug;
- a second actuator connected to the plunger; and
- a third actuator connected to the pusher.

6. The apparatus for dispensing at least one dosage of powdered material as set forth in claim 5, further comprising:
- a plurality of sensors for measuring flow and weight of the powdered material; and
- a central processing unit (CPU) for controlling the actuators to control the displacement of the chamber plug, plunger and pusher.

7. The apparatus for dispensing at least one dosage of powdered material as set forth in claim 6, wherein the actuators are programmable.

8. The apparatus for dispensing at least one dosage of powdered material as set forth in claim 7, wherein the actuator is one of a servomotor, a step motor, a pneumatic actuator and a hydraulic actuator.

9. The apparatus for dispensing at least one dosage of powdered material as set forth in claim 3, further comprising:
- a distribution chamber provided at a side of the body, the distribution chamber having an outlet,
- wherein the pusher dispenses powdered material into the distribution chamber to fill individual containers.

10. The apparatus for dispensing at least one dosage of powdered material as set forth in claim 9, wherein the distribution chamber has a venturi-type configuration, which has an intermediate narrow region located between opposite relatively wide inlet and outlet regions for improving aerodynamic characteristics of powder flow.

11. The apparatus of claim 2, wherein the plunger compacts the powdered material in the chamber against the chamber plug to evacuate air from the chamber through the perforated screen.

12. The apparatus of claim 11, wherein the compaction provides compacted material with a substantially uniform density.

* * * * *